(12) United States Patent
Stangier et al.

(10) Patent No.: US 12,263,137 B2
(45) Date of Patent: Apr. 1, 2025

(54) APPLICATOR FOR ORAL ADMINISTRATION OF A SWALLOWABLE OBJECT TO A PATIENT

(71) Applicant: ESOCAP AG, Basel (CH)

(72) Inventors: Peter Stangier, Grenzach-Wyhlen (DE); Julius Krause, Greifswald (DE); Christoph Rosenbaum, Greifswald (DE)

(73) Assignee: ESOCAP AG, Basel (CH)

( * ) Notice: Subject to any disclaimer, the term of this patent is extended or adjusted under 35 U.S.C. 154(b) by 820 days.

(21) Appl. No.: 17/438,526

(22) PCT Filed: Mar. 13, 2020

(86) PCT No.: PCT/EP2020/056927
§ 371 (c)(1),
(2) Date: Sep. 13, 2021

(87) PCT Pub. No.: WO2020/183003
PCT Pub. Date: Sep. 17, 2020

(65) Prior Publication Data
US 2022/0142870 A1 May 12, 2022

(30) Foreign Application Priority Data
Mar. 14, 2019 (EP) ..................................... 19162947

(51) Int. Cl.
*A61J 7/00* (2006.01)
*A61B 10/02* (2006.01)
(Continued)

(52) U.S. Cl.
CPC ............. *A61J 7/0046* (2013.01); *A61B 10/02* (2013.01); *A61J 3/06* (2013.01); *A61J 3/07* (2013.01);
(Continued)

(58) Field of Classification Search
None
See application file for complete search history.

(56) References Cited

U.S. PATENT DOCUMENTS 2,940,447 A 6/1960 Zanegood
3,302,644 A * 2/1967 Kennedy ............... A61J 7/0046
215/311
(Continued)

FOREIGN PATENT DOCUMENTS

FR 2697331 A1 4/1994
GB 2509918 A 7/2014
(Continued)

*Primary Examiner* — Manuel A Mendez
(74) *Attorney, Agent, or Firm* — PERRY + CURRIER (57) ABSTRACT

The application relates to an applicator (1) for oral administration of a swallowable object (2), in particular a solid dosage form, to a patient, wherein the applicator comprises a housing (3) having a first opening (4) and a second opening (5), the first opening of the housing being configured to be coupled with a liquid reservoir, in particular a drinking vessel, and the second opening of the housing being configured such that the patient can drink therefrom, and a holder (6) disposed within the housing and configured to accommodate the swallowable object, the holder being further configured to allow the swallowable object to be conveyed towards the second opening of the housing when liquid is flowing through the housing from the first opening to the second opening of the housing.

19 Claims, 7 Drawing Sheets

(51) Int. Cl.
*A61J 3/06* (2006.01)
*A61J 3/07* (2006.01)
*A61J 3/10* (2006.01)
*A61M 31/00* (2006.01)
*A61B 10/00* (2006.01)

(52) U.S. Cl.
CPC .............. *A61J 3/10* (2013.01); *A61M 31/007* (2013.01); *A61B 2010/0061* (2013.01); *A61B 2010/0216* (2013.01); *A61B 2562/162* (2013.01)

(56) References Cited

U.S. PATENT DOCUMENTS

| | | |
|---|---|---|
| 2003/0057115 A1 | 3/2003 | Langeler et al. |
| 2005/0092754 A1 | 5/2005 | Marsden et al. |
| 2005/0247719 A1 | 11/2005 | Loging |
| 2006/0293641 A1 | 12/2006 | Nishijima et al. |
| 2015/0289752 A1 | 10/2015 | Rachlin et al. |
| 2016/0045189 A1 | 2/2016 | Maguire et al. |
| 2016/0051805 A1 | 2/2016 | Scorzelli et al. |

FOREIGN PATENT DOCUMENTS

| | | |
|---|---|---|
| JP | 2003508106 A | 3/2003 |
| JP | 2009000146 A | 1/2009 |
| RU | 2013152056 A | 5/2015 |
| UA | 37559 U | 11/2008 |
| WO | WO-2013114111 A1 | 8/2013 |

\* cited by examiner

APPLICATOR FOR ORAL ADMINISTRATION OF A SWALLOWABLE OBJECT TO A PATIENT

The present invention relates to an applicator and a drinking device for oral administering of a swallowable object, in particular a solid dosage form, to a patient.

In recently developed methods for diagnosis of the upper gastrointestinal tract the patient has—as an alternative to using an endoscope—just to swallow a small object, which is designed as a single-use device which is configured to collect cells from the lining of the esophagus. The device comprises a small mesh sponge, about 30 mm in diameter, contained in a gelatin capsule and attached to a string or thread. The patient swallows the capsule with water, and the gelatin coating dissolves once the device reaches the stomach. After a few minutes, the health care provider uses the string to retrieve the expanded sponge. While being retrieved, the slightly abrasive mesh collects cells along the length of the esophagus. The collected cells can then be analyzed, e.g. by using immuno-histochemical staining to detect biomarkers indicating particular diseases.

Although swallowing small objects, like capsules, is usually less inconvenient for patients compared to using other diagnostic devices such as endoscopes, it is desirable to make oral administering of such objects as convenient and reliable as possible.

It is an object of present invention to provide an applicator and a drinking device allowing for an oral administering of a swallowable object to a patient in a convenient and reliable manner.

The object is achieved by the applicator and the drinking device according to the independent claims.

According to a first aspect of the invention, an applicator for oral administering of a swallowable object, in particular a solid dosage form, to a patient, comprises a housing having a first opening and a second opening, the first opening of the housing being configured to be coupled with a liquid reservoir, in particular a drinking vessel, and the second opening of the housing being configured such that the patient can drink therefrom. The applicator further comprises a holder disposed within the housing and configured to accommodate the swallowable object, the holder being further configured to allow the swallowable object to be conveyed towards the second opening of the housing when liquid is flowing through the housing from the first opening to the second opening of the housing.

According to a second aspect of the invention, a drinking device comprises an applicator according to the first aspect of the invention, and a vessel, in particular a drinking vessel, configured to contain a liquid, wherein the applicator is, in particular releasably, coupled with the vessel such that liquid contained in the vessel can enter the applicator via the first opening of the housing.

Aspects of the invention are based on the approach to accommodate and/or store and/or hold a swallowable object or device, which preferably has the shape and/or size of, e.g., a capsule, pill, tablet or pellet, within a, preferably sleeve-like or tubular, housing by means of a holder disposed within the housing. The applicator, in particular the housing, is formed and/or dimensioned and/or configured such that it can be coupled with and/or attached to a liquid reservoir, e.g. a drinking vessel, and allows liquid contained in the reservoir, in particular after or while tilting the vessel together with the applicator attached thereto, to flow through the housing and/or holder from a first opening towards a second opening of the housing. Preferably, the second opening of the housing is dimensioned and/or shaped, e.g., like a spout, a beak-shaped spout or a mouthpiece of a feeding cup such that a patient can drink therefrom conveniently. Further, the holder is preferably configured such that it releases the accommodated swallowable object when the applicator is being tilted and/or liquid is flowing through the housing and allows the swallowable object to be conveyed by gravitation and/or by the liquid flowing through the housing towards the second opening of the housing, where it exits the housing together with liquid so that it can be easily swallowed by the patient.

Preferably, the swallowable object is or comprises at least one of the following solid or semi-solid dosage forms: tablet, film-coated tablet, caplet, dragée, soft gelatin capsule, hard gelatin capsule, effervescent tablet, pill, powder, granule, pellet, paste, cream, ointment, gel.

Preferably, the swallowable object or device is a solid dosage form like a capsule to which a string and/or thread is attached. Preferably, the applicator is configured to accommodate both the object and the string or thread attached thereto. For example, the string or thread may be at least partially coiled and disposed within the housing and/or the holder and/or around the holder. Alternatively or additionally, at least a section of the string or thread may be coiled around the solid dosage form and/or disposed within the solid dosage form, e.g. the capsule. In any of the aforementioned cases, the applicator and/or the holder and/or the dosage form is preferably configured to release the string or thread to allow the solid dosage form to follow gravitation and/or the liquid flowing through the housing towards the second opening and to be swallowed by the patient.

In this way, the invention allows for a convenient and reliable oral administering of swallowable objects, like solid dosage forms, to a patient.

According to a preferred embodiment, the holder comprises a holder structure being, in particular coaxially, disposed within the housing and configured to accommodate the swallowable object. Preferably, the holder structure comprises a bottom structure being provided at a first end of the holder structure. Further, it is preferred that the bottom structure is configured to allow at least a part of the liquid, which is flowing through the housing from the first opening to the second opening of the housing, to flow through the holder structure and to thereby convey the swallowable object towards the second opening of the housing. By means of one or more of the aforementioned preferred embodiments, an accommodation of the swallowable object within the applicator, on the one hand, and release and conveyance of the swallowable object towards the second opening of the applicator housing, on the other hand, is ensured in a particularly reliable and simple way.

It is further preferred that the bottom structure comprises and/or is designed as a grid. Preferably, the grid has a grid structure which is smaller than the smallest dimension, e.g. a diameter, of the swallowable object, such that the swallowable object cannot pass the grid. In this way it is ensured that the swallowable object accommodated by the holder and/or resting on the grid cannot pass the grid and enter the liquid reservoir, e.g. a drinking vessel, provided at the first opening of the applicator housing, whereas liquid from the reservoir can pass the grid in the opposite direction and "wash away" the swallowable object from the grid towards the second opening of the applicator housing.

The term "grid" or "grid structure" within the meaning of present disclosure preferably, but not necessarily, relates to a lattice and/or a framework or structure of two or more crossing strip-like elements. In a very simple example, a grid or grid structure may be formed by only two crossing strip-like elements.

Alternatively or additionally, it is preferred that the bottom structure comprises and/or is designed as a bridge, bridge-like or strip-like support structure which is configured to accommodate and/or support the swallowable object from below to ensure that the swallowable object resting on the bridge, bridge-like or strip-like support structure, respectively, cannot enter the liquid reservoir, and to allow at least a part of the liquid, which is flowing through the housing from the first opening to the second opening of the housing, to flow past the bridge, bridge-like or strip-like support structure, respectively, and to thereby convey the swallowable object towards the second opening of the housing.

According to yet another preferred embodiment, the bottom structure is mounted on and/or attached to the housing. Preferably, the bottom structure is mounted on or attached to the inside of the housing close to the first opening of the housing. In this way, liquid entering the housing and passing the holder via the bottom structure of the holder can be prevented from also entering a space between the holder structure and the inside of the housing. In this way, a thread attached to the swallowable object and stored in the space between the holder structure and the housing can be protected from contact with the liquid as long as possible so that, for example, the thread comes into contact with the liquid only, or not significantly earlier than, when the object, together with the liquid, is being swallowed by the patient. This is of particular advantage, e.g., in cases where the thread carries a drug or any other substance intended to be released at the esophagus, because preventing liquid to contact the thread too early ensures that the drug is not washed out from the thread prior to reaching the esophagus.

For example, the bottom structure may be provided with a flange by which it is mounted on the housing. Alternatively, the housing and the holder and/or the bottom structure may be formed as a single piece obtained by a suitable manufacturing method, e.g. injection molding or 3D printing.

It is further preferred that the holder structure comprises a wall structure, which is in particular attached to the bottom structure, wherein the wall structure exhibits one or more notches, slots and/or recesses allowing a thread or string, which is attached to the swallowable object accommodated within the holder structure, in particular within the wall structure, to be guided from within the holder structure or wall structure, respectively, to the outside of the wall structure and/or vice versa, i.e. from outside of the wall structure to the inside of the wall structure, and/or to be coiled around the outside of the wall structure. Preferably, the holder structure further comprises at least one fixing element, which is in particular provided at the outside of the wall structure, configured to allow the thread to be fixed at the holder structure. For example, the fixing element may be or comprise a protrusion provided at the outside of the wall structure and formed and/or dimensioned such that the thread or string can be knotted thereon. The aforementioned embodiments, alone or in combination, allow for a safe accommodation of both the swallowable object, e.g. a dosage form, and the attached thread or string by the holder.

As already mentioned above, the string or thread may not necessarily be coiled around the holder or holder structure. Alternatively or additionally, at least a section of the string or thread may be coiled around the swallowable object, e.g. a solid dosage form like a capsule, and/or disposed within the swallowable object.

According to yet another preferred embodiment, the applicator further comprises and/or includes the swallowable object, in particular a solid dosage form, which is accommodated by the holder. Alternatively or additionally, the applicator further comprises at least one cap configured to seal the first opening of the housing and/or the second opening of the housing, wherein the at least one cap is releasably attached to the first opening and/or second opening of the housing. Prior to administering the swallowable object contained in the applicator to a patient, the at least one cap is detached from the opening(s) of the housing. In the aforementioned embodiments the applicator advantageously also serves as a primary packaging for the swallowable object, in particular the solid dosage form, contained therein. For hygienic purposes, the applicator may be preferably packed into an additional outer or secondary packaging, e.g. a plastic bag or a box, which may be labelled, e.g., with a brand name and/or information regarding the contained object and/or instructions for using the applicator.

It is further preferred that the vessel has an opening and that the applicator is, in particular releasably and/or detachably, attached to the opening of the vessel. For example, the vessel can be a conventional drinking vessel, like a drinking glass or cup, to which the applicator is attached. Alternatively, the vessel can be a drinking vessel having a screw-cap which is provided with a nozzle or spout on which the applicator is, preferably releasably and/or detachably, attached.

As already described above, the swallowable object can preferably be a single-use device which is configured to collect cells from the lining of the esophagus and comprises a small mesh sponge contained in a gelatin capsule and attached to a string.

Basically, topical treatment in the upper gastrointestinal tract is difficult to achieve due to short esophageal transit times with less than two seconds from the mouth to the stomach. In view of these limitations, it is particularly preferred that the swallowable object comprises a solid dosage form, like a capsule, pill, tablet or pellet, attached to a thread or string which is configured for topical treatment of the esophagus. For example, the thread or string may contain a drug or any other substance. By swallowing the solid dosage form, the preferably drug-carrying thread or string attached thereto is guided through the esophagus and can dwell in the esophagus for a desired period of time, e.g. in order to ensure that the drug is released by the thread or string and delivered to the esophagus.

Preferably, the term "thread" within the meaning of present disclosure does not necessarily have to be a thread in the narrower sense, but may also be or comprise a film, also referred to as "wafer", "thin strip", "edible film" or "oral film", which is a preferably thin, flexible and rapidly disintegrating drug carrier which, in contact with saliva, dissolves and releases an active ingredient to act either locally and/or—after absorption—also systemically.

Further advantages, features and examples of the present invention will be apparent from the following description of following figures:

FIGS. 4 *a*) to *e*) show exemplary steps of using an applicator;

FIGS. 5 a) to d) show exemplary steps of assembling an applicator;

FIGS. 6 a) to c) show an example of a holder in various perspective views;

FIGS. 10 a) and b) show another example of an applicator in a front view and a perspective view, respectively; and FIGS. 11 a) and b) show another example of an applicator in a front view and a perspective view, respectively.

Figure 1:
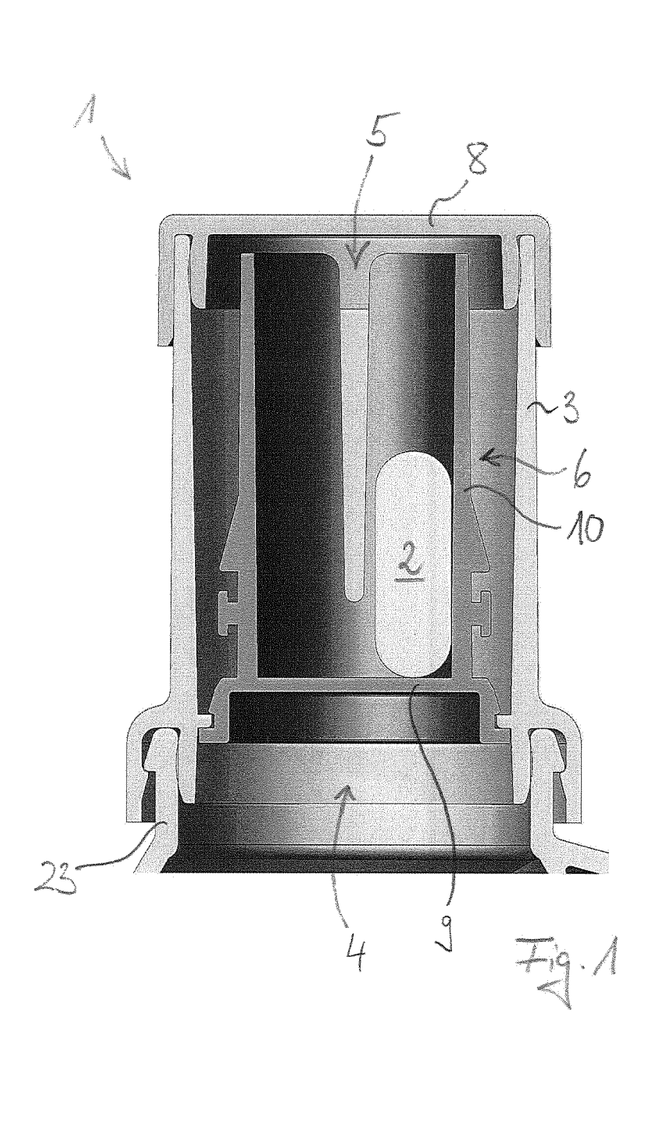
FIG. 1 shows a cross-section of an example of an applicator in a front view.

FIG. 1 shows a cross-section of an example of an applicator 1 in a front view. The applicator 1 comprises a housing 3 exhibiting a preferably sleeve-like and/or rotationally symmetric shape and having a first opening 4 and a second opening 5. Preferably, in the region of and/or close to its first opening 4, the housing 3 is formed and/or configured such that it can be, preferably liquid-tightly, coupled with and/or attached to an upper end and/or opening 23 of a liquid reservoir, in particular a drinking vessel such as a drinking bottle.

The applicator 1 further comprises a holder 6 which is disposed within the housing 3 and shaped and/or configured to accommodate and/or hold and/or retain a swallowable object 2. Preferably, the swallowable object 2 has a size and a shape of a solid dosage form such as a capsule. In present example, the swallowable object 2 is supported both from below and laterally by bottom structure 9 and wall structure 10, respectively, of the holder 6. Further, in the given example, a detachable cap 8 is attached to the second opening 5 of the housing 3 in order to seal the second opening 5.

Figure 2:
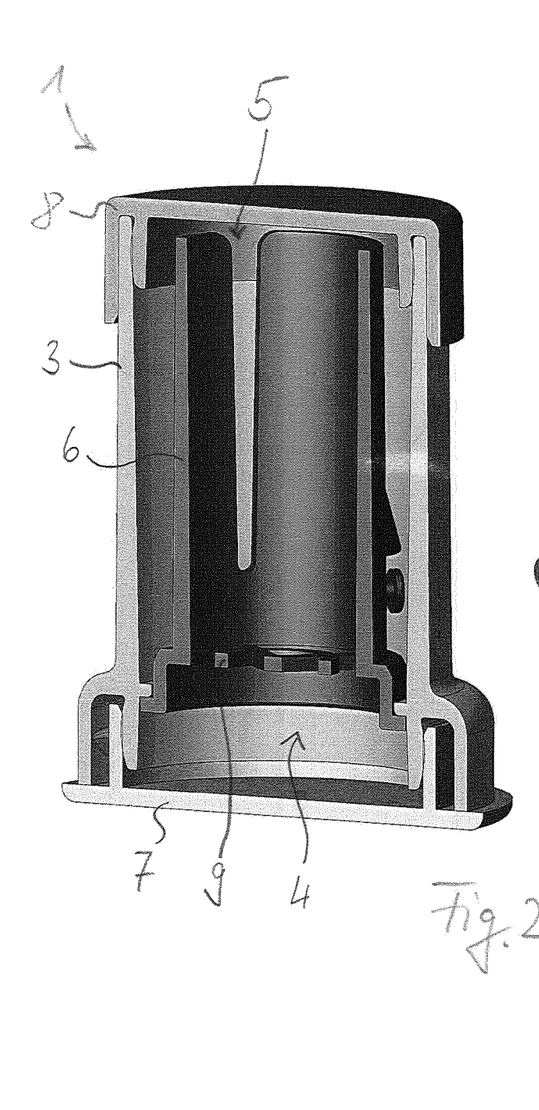
FIG. 2 shows a cross-section of an example of an applicator in a perspective view.

FIG. 2 shows a cross-section of an example of an applicator 1 in a perspective view. Like with the example given in FIG. 1, the second opening 5 of the housing 3 is sealed with a cap 8. However, rather than being attached to a drinking vessel, the first opening 4 is also sealed with a cap 7, which is detachably attached thereto. Preferably, the bottom structure 9 of the holder 6 is permeable to liquid and may be, for example, configured as a grid or any other structure which is permeable to liquid.

Preferably, the housing 3 and/or the holder 6 has or have a sleeve-like or tubular basic form and/or the housing 3 and/or the holder 6 is or are rotationally symmetric. Preferably, the holder 6 is disposed coaxially within the housing 3, i.e. the axes of rotational symmetry of the holder 6 and the housing 3 coincide.

Figure 3:
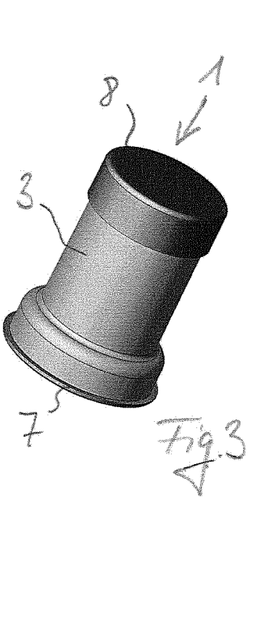
FIG. 3 shows an example of an applicator in a perspective view.

FIG. 3 shows an example of an applicator 1 in a perspective view, where the housing 3 is sealed by both a bottom cap 7 and a top cap 8.

As can be seen from the examples of FIGS. 2 and 3, the applicator 1 may advantageously serve as a primary packaging for the swallowable object 2, in particular the solid dosage form, contained therein. For hygienic purposes, the applicator 1 may preferably packed into an additional outer or secondary packaging, e.g. a plastic bag or a box (not shown).

Prior to administering the swallowable object 2 contained in the applicator 1 to a patient, the caps 7, 8 are detached from the openings 4, 5 and the housing 3 is attached to an opening 23 of a liquid reservoir. This will be explained in more detail in the following.

FIGS. 4 a) to e) show exemplary steps of using an applicator 1 in a cross-sectional representation.

Figure 4A:
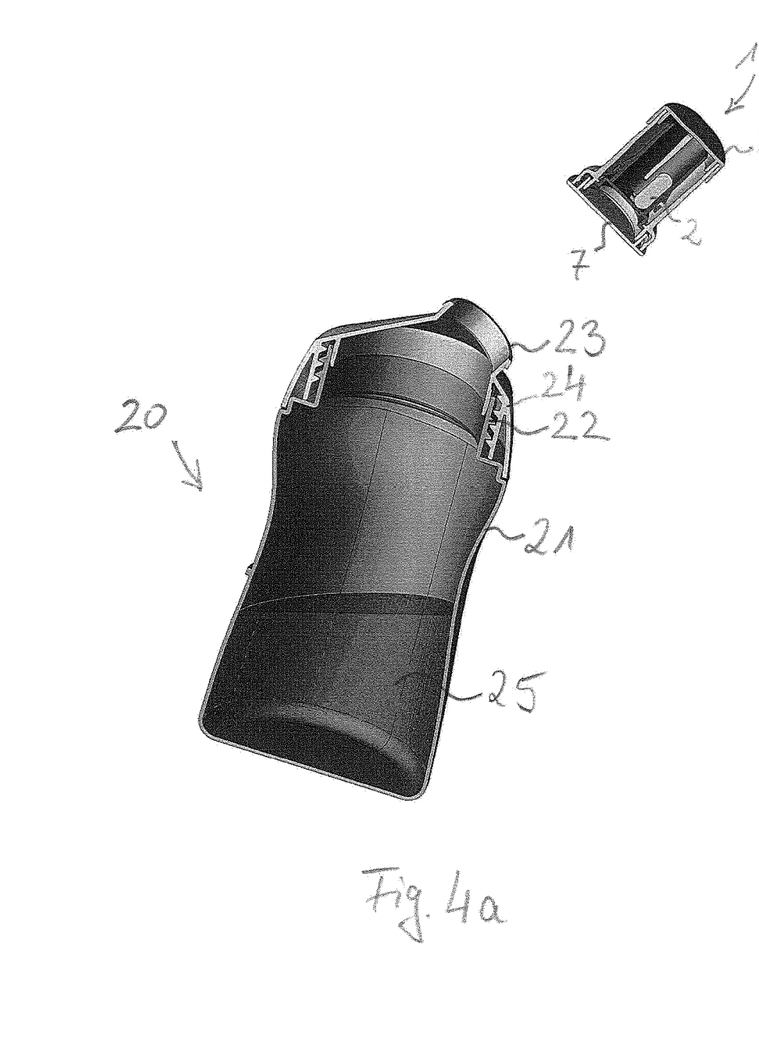
Figure 4B:
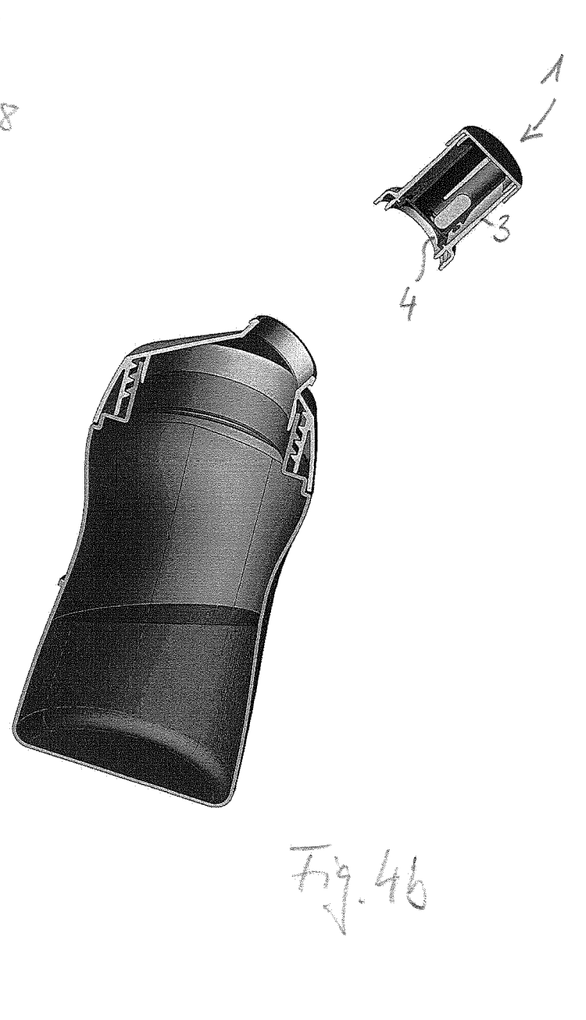

In a first step shown in FIG. 4a, an applicator 1 containing a swallowable object 2 and being sealed with the caps 7, 8 as well as a drinking vessel 20 are provided. In present example, the drinking vessel 20, which is filled with liquid 25, such as water, comprises a cup 21 having a threaded coupling 22 at its top opening. A screw cap 24 having an opening 23 is screwed onto the threaded coupling 22. The opening 23 of the screw cap 24 is preferably configured, in particular shaped and/or dimensioned, such that a person can drink therefrom. Preferably, the drinking vessel 20 including cup 21 and screw cap 24 with opening 23 is a drinking vessel which is commonly used in the field of healthcare, like in hospitals or medical practices.

Figure 4C:
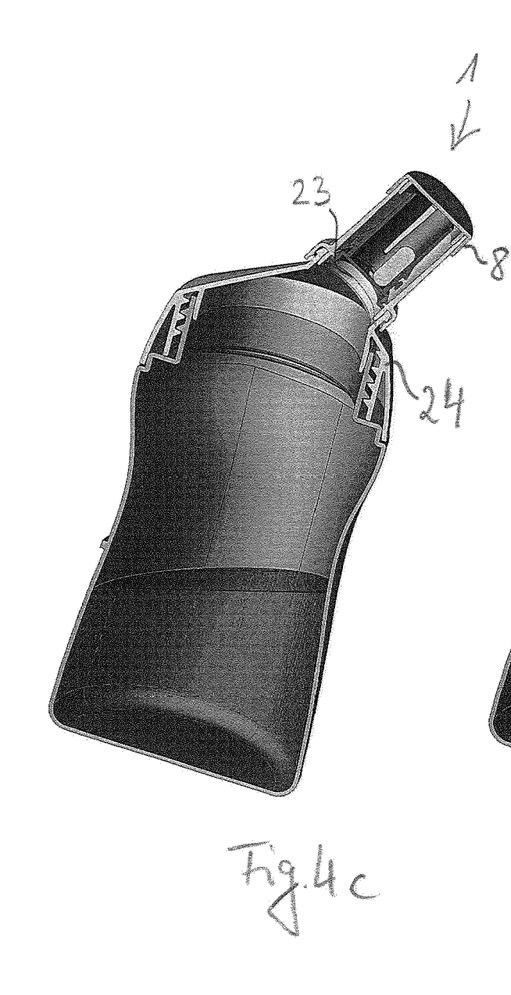
Figures 4D, 4E:
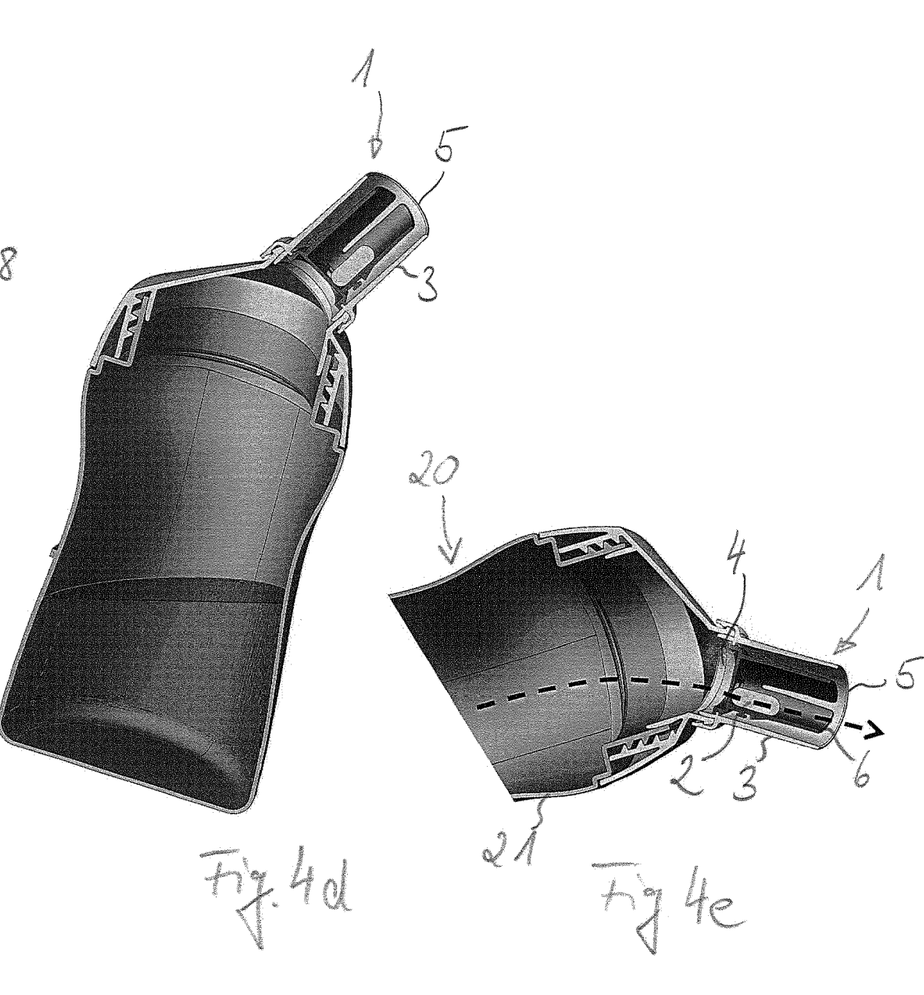

In a second and third step, the bottom cap 7 at the first opening 4 of the housing 3 of the applicator 1 is removed (FIG. 4b), and the applicator 1 is attached to the opening 23 of the screw cap 24 (FIG. 4c). In a fourth step (FIG. 4d), the top cap 8 at the second opening 5 of the housing 3 of the applicator 1 is removed.

In a fifth step (FIG. 4e), the drinking vessel 20 together with the applicator 1 attached thereto is tilted to allow liquid to flow (indicated by dashed arrow) out of the cup 21 through the first opening 4 of the housing 3 and, subsequently, at least partially through the holder 6 accommodating the swallowable object 2. Due to the liquid flowing through the holder 6 and/or gravitation, the swallowable object 2 is conveyed towards the second opening 5 of the housing 6, where it is "washed away" by the liquid flowing out of the second opening 5 and can be swallowed by the patient drinking from the second opening 5.

FIGS. 5 a) to d) show exemplary steps of assembling an applicator 1 in a cross-sectional view.

In a first step (FIG. 5a), a holder 6 is provided. In a second step (FIG. 5b), a swallowable object 2 is inserted into and/or placed within the holder 6 such that the swallowable object 2 is preferably supported by the bottom structure 9 of the holder 6 and/or preferably abuts the wall structure 10 of the holder 6. Preferably, the swallowable object 2 is a dosage form, e.g. a capsule, pill or tablet, to which a thread or string (not shown) is attached with a first end of the thread or string.

Figure 5A:
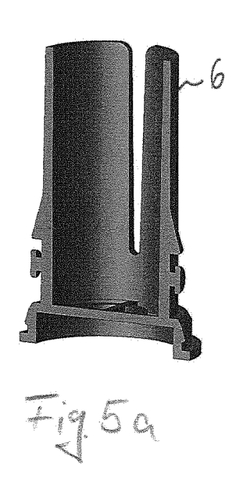
Figure 5B:
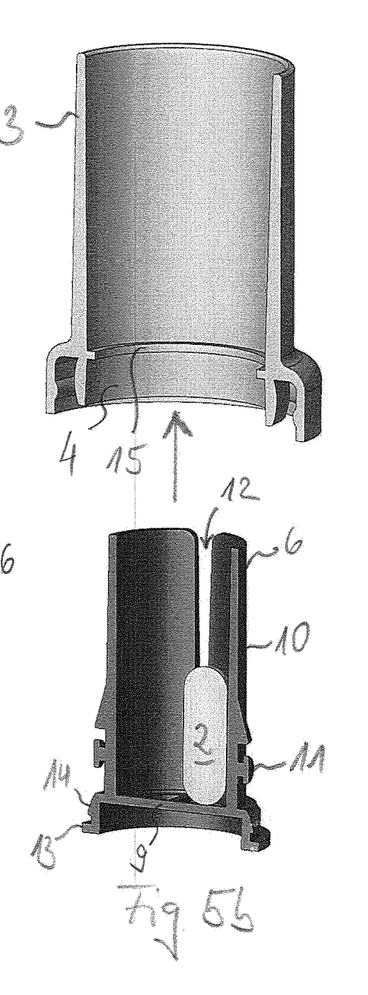
Figure 5C:
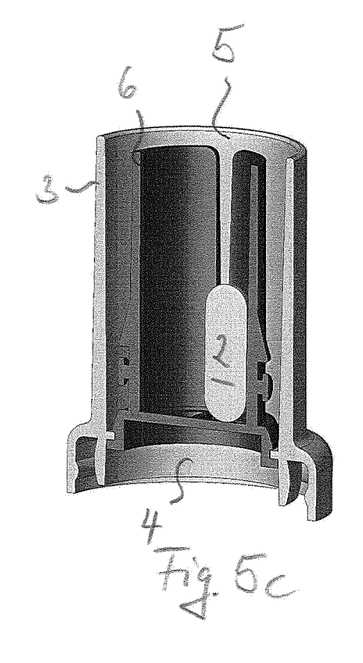
Figure 5D:
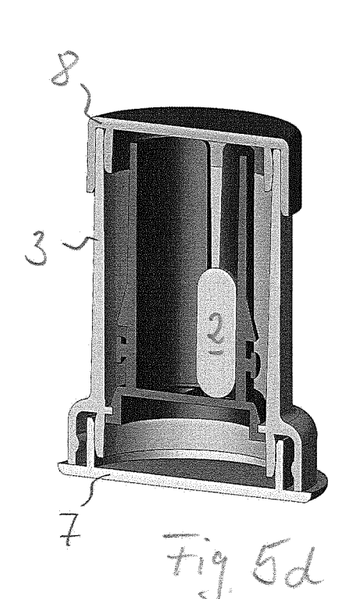

Preferably, prior to inserting the object 2 into the holder 6, the thread is inserted into and/or laid on or along the holder 6. For example, the thread may be laid in the shape of an "8" through and around the holder 6 by repeating the following sequence: i) winding the thread around a first half of the wall structure 10, ii) guiding the thread via two opposing notches 12 provided in the wall structure 10 through the interior of the holder 6, iii) winding the thread around a second half of the wall structure 10, and iv) guiding the thread via the two opposing notches 12 through the interior of the holder 6.

Preferably, the second end of the thread or string, which is not attached to the object 2, may be fixed on a fixing element 11 provided at the outside of the wall structure 10. Alternatively or additionally, the fixing element 11 or any other similarly acting element for fixing the thread may be provided at another position at the holder 6 and/or the housing 3, e.g. at the bottom structure 9 and/or at the inside of the wall structure 10.

In a third step (see arrow in FIG. 5b), the holder 6 together with the object 2 accommodated therein is pushed into the housing 3. Preferably, at the bottom region of the holder 6 a flange 13 and a slanted protrusion 14 are provided. It is further preferred that, in proximity of the first opening 4 of the housing 3, a circumferential rib 15 which fits in between the flange 13 and the protrusion 14 is provided. Preferably, when inserting the holder 6 into the housing 3 from below, the slanted protrusion 14 can pass the rib 5 in the direction indicated by the arrow, but acts as a barb in the opposite direction so that the holder 6 is fixed at the inner wall of the housing 6 by means of form-fit of the rib 15 between the flange 13 and the protrusion 14. This is illustrated by in FIG. 5c.

In a fourth and fifth step (see FIG. 5d), an upper cap 8 and a lower cap 7, respectively, is attached to the housing 3 to seal the second opening 5 and first opening 4, respectively, of the housing 3.

Figure 6A:
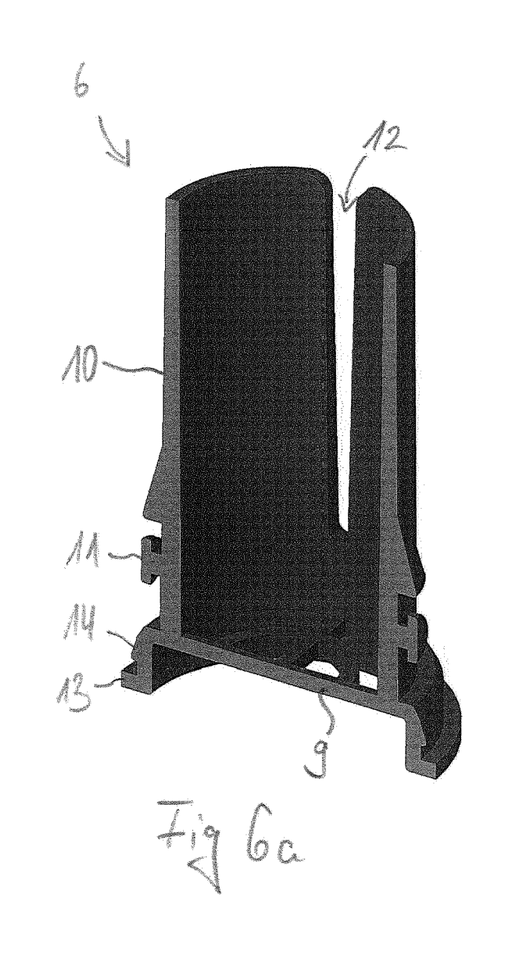
Figure 6B:
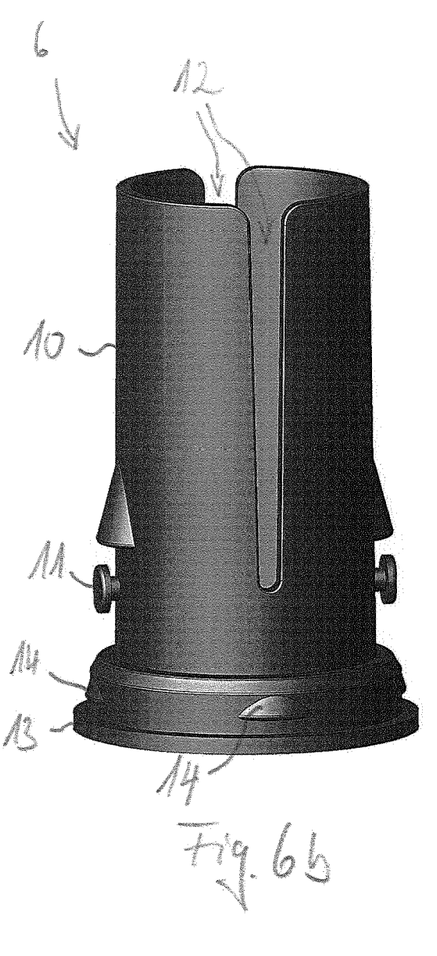
Figure 6C:
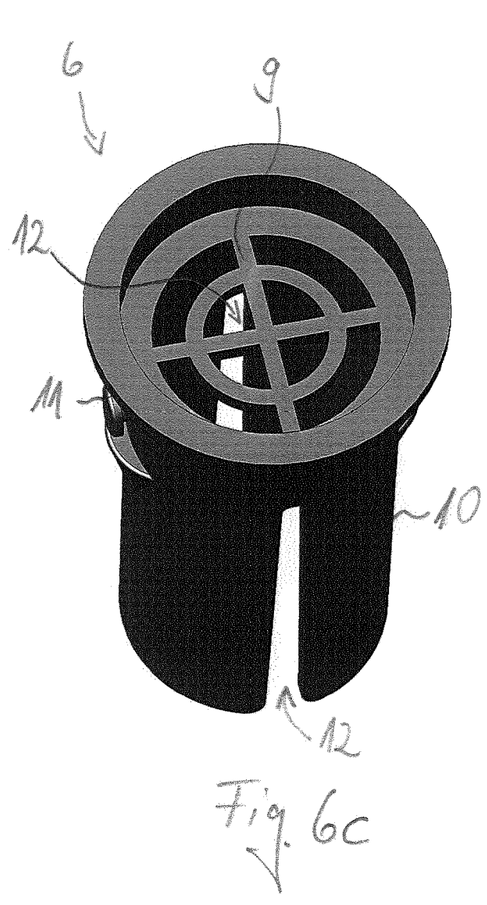

FIGS. 6 a) to c) show various perspective views of an example of a holder 6, wherein FIG. 6a shows a cross-section of the holder 6. Basically, regarding bottom structure 9, wall structure 10, fixing elements 11, notches 12, flange 13 and protrusions 14, the above elucidations apply accordingly.

As can be seen from FIGS. 6b and 6c, in present example two notches 12 are provided at opposing sides of the wall structure 12. In general, it is possible to provide less or more than two notches 12, e.g. four notches distributed in 90° steps around the wall structure 12.

As apparent from FIGS. 6a and 6c, the bottom structure 9 of the holder 9 has a crosshair-like structure, which efficiently prevents an object 2 accommodated within the holder 6 to pass the bottom structure 9 and to enter the liquid reservoir. In general, it is possible to provide any other type of grid which is permeable to liquids, on the one hand, and prevents the accommodated object 2 from passing the bottom structure 9 towards the liquid reservoir, on the other hand. Preferably, the bottom structure 9 has apertures which are smaller than the cross-section of the object 2, in particular a dosage form, accommodated within the holder 6.

In the following, further examples of an applicator 1 are described with reference to figures which only show particular aspects of the applicator 1, while further details are neglected for sake of simplification. It should be understood, however, that (not shown) details of the following examples may be at least partially designed like in the examples of an applicator 1 discussed above.

Figure 7:
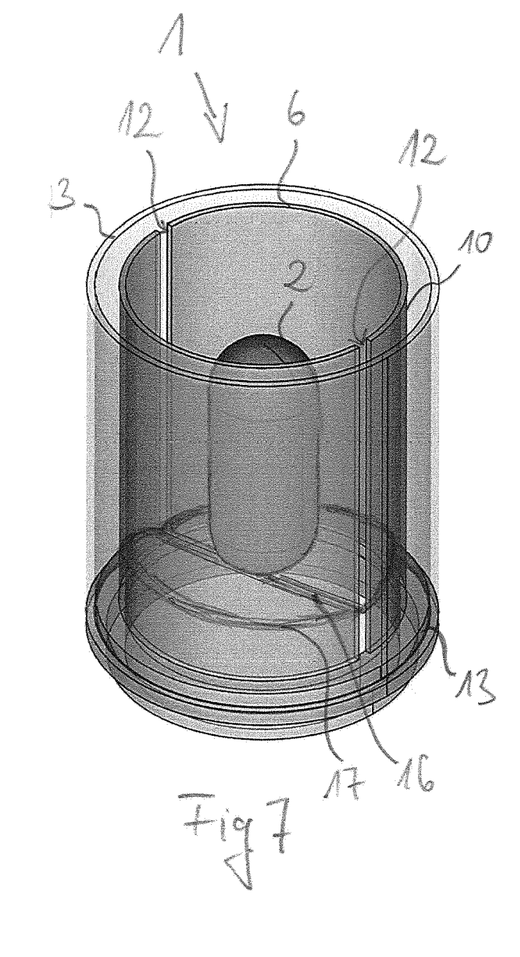
FIG. 7 shows another example of an applicator in a perspective view.

FIG. 7 shows another example of an applicator in a perspective view. The housing 3 has an essentially tubular or sleeve-like basic shape and is slipped onto a flange structure 13 of the holder 6 to engage frictionally and/or by form-fit with the holder 6.

Like with the examples given above, in the circumferential wall structure 10 of the holder 6 two notches 12 are provided. In present example, the notches 12 extend from the upper end of the wall structure 10 to the lower end of the wall structure 10, where the flange structure 13 is provided.

Further, in present example, the swallowable object 2 accommodated within the holder 6 is supported by and/or lies on a web, path or bridge 16 formed by a plurality of sections of a thread 17 which is attached to the swallowable object 2 and has been repeatedly guided, via the notches 12, through the interior of the holder 3 and around the outside of the holder 6. In present example, as indicated in the figure, the thread is laid in a shape resembling an "8". In this respect, the above elucidations with reference to FIG. 5b apply accordingly.

It is further preferred that one end of the thread 17 is attached to the object 2, while the other end of the thread 17 is affixed to the applicator 1, preferably by jamming the end of the thread 17 between the housing 3 and the flange structure 13 of the holder 6 when slipping the housing 3 onto the flange structure 13 of the holder 6.

Figure 8:
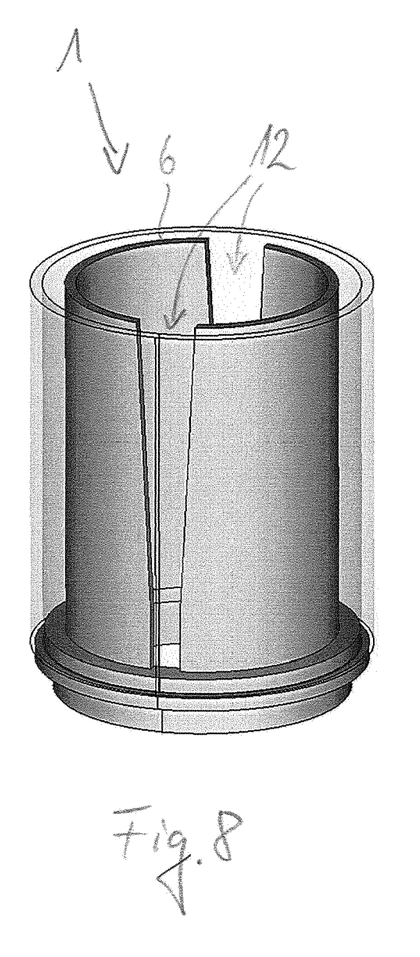
FIG. 8 shows another example of an applicator in a perspective view.

FIG. 8 shows another example of an applicator 1 in a perspective view. Basically, the above elucidations given with reference to FIG. 7 apply accordingly. In distinction to the example given in FIG. 7, where the notches 12 have an essentially fixed width, however, the width of the notches 12 in present example increases towards the upper end of the holder 6. Preferably, the notches 12 have a trapezoidal shape. In this way, unwinding of the thread 17 from the holder 6 is enabled in a particularly reliable manner.

Figure 9:
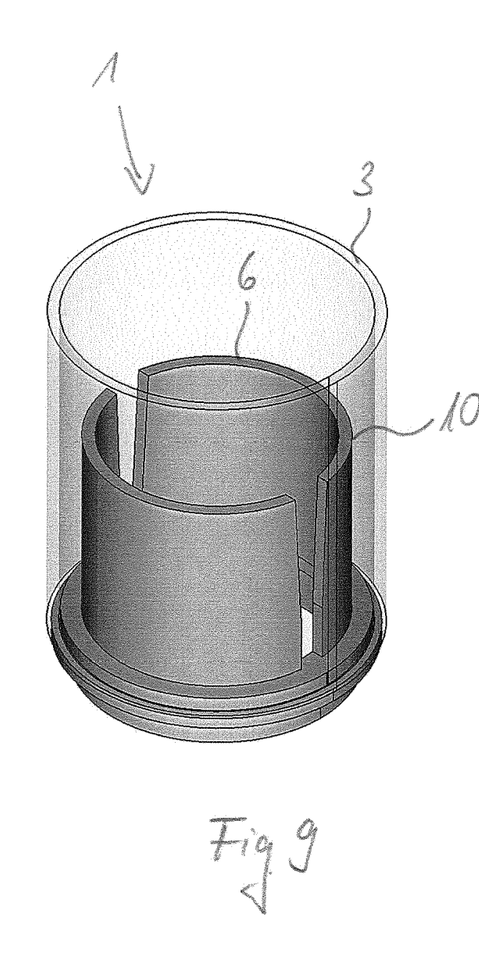
FIG. 9 shows another example of an applicator in a perspective view.

FIG. 9 shows another example of an applicator 1 in a perspective view. Basically, the above elucidations given with reference to FIG. 8 apply accordingly. In distinction to the example given in FIG. 8, the height of the wall structure 10 of the holder 6 is reduced. Preferably, the height of the wall structure 10 corresponds to approx. 30 to 80%, preferably 50 to 60%, of the height of the housing 3. In this way, unwinding of the thread 17 from the holder 6 is further facilitated.

Figure 10A:
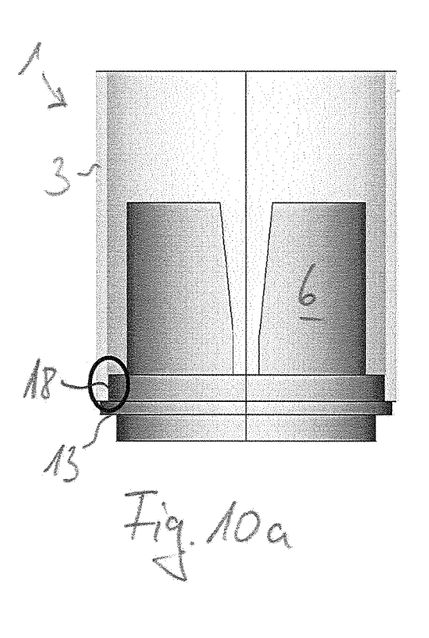
Figures 10B, 11A:
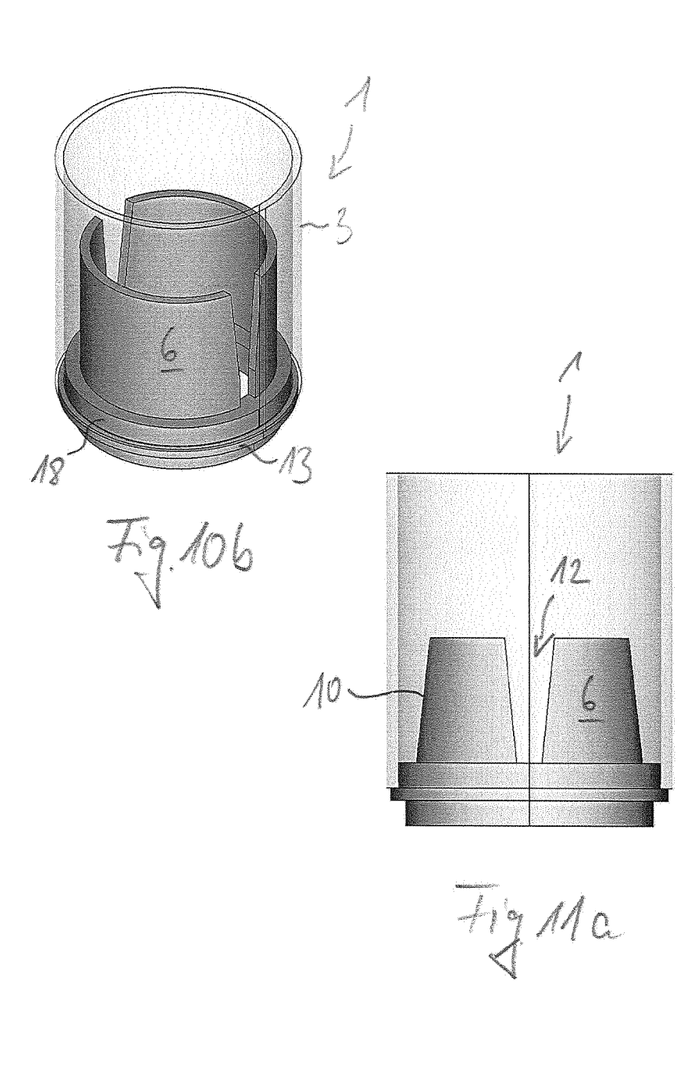

FIGS. 10a) and b) show another example of an applicator in a front view and a perspective view, respectively. Basically, the above elucidations given with reference to FIG. 9 apply accordingly. In distinction to the example given in FIG. 9, the height of a step 18 adjoining the flange 13 has been increased in order to ensure an even more stable fixation of the housing 3 and the holder 6.

Figure 11B:
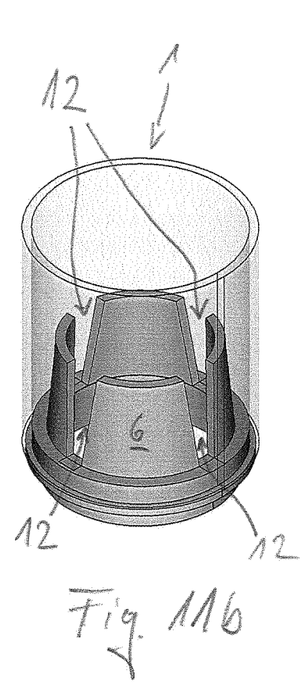

FIGS. 11 a) and b) show another example of an applicator in a front view and a perspective view. Basically, the above elucidations given with reference to FIG. 10 apply accordingly. In distinction to the example given in FIG. 10, the wall structure 10 exhibits an essentially conical basic form with in total four notches 12, allowing for a particularly reliable unwinding of the thread (not shown) from the holder 6.

The invention claimed is:

1. An applicator (1) for oral administering of a swallowable object (2), in particular a solid dosage form, to a patient, the applicator (1) comprising:
    a housing (3) having a first opening (4) and a second opening (5), the first opening (4) of the housing (3) being configured to be coupled with a liquid reservoir (20), in particular a drinking vessel, and the second opening (5) of the housing (3) being configured such that the patient can drink therefrom, and
    a holder (6) disposed within the housing (3) and configured to accommodate the swallowable object (2), the holder (6) being further configured to allow the swallowable object (2) to be conveyed towards the second opening (5) of the housing (3) when liquid (25) is flowing through the housing (3) from the first opening (4) to the second opening (5) of the housing (3),
    the holder (6) comprising a holder structure (9-14) being, in particular coaxially, disposed within the housing (3) and configured to accommodate the swallowable object (2), and
    the holder structure (9-14) comprising a wall structure (10), the wall structure (10) exhibiting one or more notches, slots and/or recesses (12) allowing a thread or string (17), which is attached to the swallowable object (2) accommodated within the wall structure (10), to be guided from within the wall structure (10) to the outside of the wall structure (10) or vice versa and/or to be coiled around the outside of the wall structure (10).

2. The applicator (1) according to claim 1, the holder structure (9-14) comprising a bottom structure (9) being provided at a first end of the holder structure (9-14).

3. The applicator (1) according to claim 2, the bottom structure (9) being mounted on and/or attached to the housing (3).

4. The applicator (1) according to claim 2, wherein the wall structure (10), is attached to the bottom structure (9).

5. The applicator (1) according to claim 4, the holder structure (9-14) further comprising at least one fixing element (11) configured to fix the thread (17) at the holder structure (9-14).

6. The applicator (1) according to claim 2, the holder structure (9-14) comprising a wall structure (10), which is in particular attached to the bottom structure (9), the wall structure (10) exhibiting one or more notches (12) allowing a thread (17), which is attached to the swallowable object (2) accommodated within the wall structure (10), to be guided from within the wall structure (10) to the outside of the wall structure (10) or vice versa and/or to be coiled around the outside of the wall structure (10).

7. The applicator (1) according to claim 6, the holder structure (9-14) further comprising at least one fixing element (11) configured to fix the thread (17) at the holder structure (9-14).

8. The applicator (1) according to claim 2, the bottom structure (9) being configured to allow at least a part of the liquid (25), which is flowing through the housing (3) from the first opening (4) to the second opening (5) of the housing (3), to flow through the holder structure (9-14) and to thereby convey the swallowable object (2) towards the second opening (5) of the housing (3).

9. The applicator (1) according to claim 8, the bottom structure (9) being mounted on and/or attached to the housing (3).

10. The applicator (1) according to claim 8, the holder structure (9-14) comprising a wall structure (10), which is in particular attached to the bottom structure (9), the wall structure (10) exhibiting one or more notches (12) allowing a thread (17), which is attached to the swallowable object (2) accommodated within the wall structure (10), to be guided from within the wall structure (10) to the outside of the wall structure (10) or vice versa and/or to be coiled around the outside of the wall structure (10).

11. The applicator (1) according to claim 10, the holder structure (9-14) further comprising at least one fixing element (11) configured to fix the thread (17) at the holder structure (9-14).

12. The applicator (1) according to claim 8, the bottom structure (9) comprising a grid and/or a bridge-like or strip-like support structure.

13. The applicator (1) according to claim 12, the bottom structure (9) being mounted on and/or attached to the housing (3).

14. The applicator (1) according to claim 12, the holder structure (9-14) comprising a wall structure (10), which is in particular attached to the bottom structure (9), the wall structure (10) exhibiting one or more notches (12) allowing a thread (17), which is attached to the swallowable object (2) accommodated within the wall structure (10), to be guided from within the wall structure (10) to the outside of the wall structure (10) or vice versa and/or to be coiled around the outside of the wall structure (10).

15. The applicator (1) according to claim 14, the holder structure (9-14) further comprising at least one fixing element (11) configured to fix the thread (17) at the holder structure (9-14).

16. The applicator (1) according to claim 1, the applicator (1) further comprising a swallowable object (1), in particular a solid dosage form, which is accommodated by the holder (6).

17. The applicator (1) according to claim 1, the applicator (1) further comprising at least one cap (7, 8) configured to seal the first opening (4) of the housing (3) and/or the second opening (5) of the housing (3), wherein the at least one cap (7, 8) is releasably attached to the first opening (4) and/or second opening (5) of the housing (3).

18. A drinking device comprising an applicator (1) according to claim 1, and a vessel (20), in particular a drinking vessel, configured to contain a liquid (25), the applicator (1) being, in particular releasably, coupled with the vessel (20) such that liquid (25) contained in the vessel (20) can enter the applicator (1) via the first opening (4) of the housing (3).

19. The drinking device according to claim 18, the vessel (20) having an opening (23) and the applicator (1) being, in particular releasably, attached to the opening (23) of the vessel (20).

* * * * *